United States Patent [19]

Fladlien

[11] Patent Number: 4,595,257
[45] Date of Patent: Jun. 17, 1986

[54] SUPPORT MECHANISM UTILIZING FLEXUAL PIVOTS

[75] Inventor: David G. Fladlien, Los Gatos, Calif.

[73] Assignee: ITP, Inc., Sunnyvale, Calif.

[21] Appl. No.: 495,618

[22] Filed: May 18, 1983

[51] Int. Cl.[4] .............................. G02B 7/04; F16F 1/00
[52] U.S. Cl. ...................................... 350/255; 74/581; 267/181
[58] Field of Search ................ 350/255, 288, 518–519, 350/632, 633–634, 636; 369/45; 267/160, 163, 165, 181; 74/519, 581; 16/225; 248/178, 324; 308/2 A

[56] References Cited

U.S. PATENT DOCUMENTS

| 1,893,098 | 1/1933 | Murray, Sr. et al. | 267/165 |
| 3,184,197 | 5/1965 | Aller | 74/519 |
| 3,583,792 | 6/1971 | Jones et al. | 350/255 |
| 3,915,560 | 10/1975 | Levine et al. | 350/255 |

FOREIGN PATENT DOCUMENTS 624331 6/1949 United Kingdom ................ 350/255

Primary Examiner—William H. Punter
Attorney, Agent, or Firm—Majestic, Gallagher, Parsons & Siebert

[57] ABSTRACT

Flexual pivots are utilized as part of supporting elements in a mechanism requiring a high degree of precision of movement over an extremely small distance. An example illustrated is for a microscope used in viewing micropatterns on an integrated circuit chip wherein a focusing element is supported by such a flexual pivot structure.

2 Claims, 4 Drawing Figures

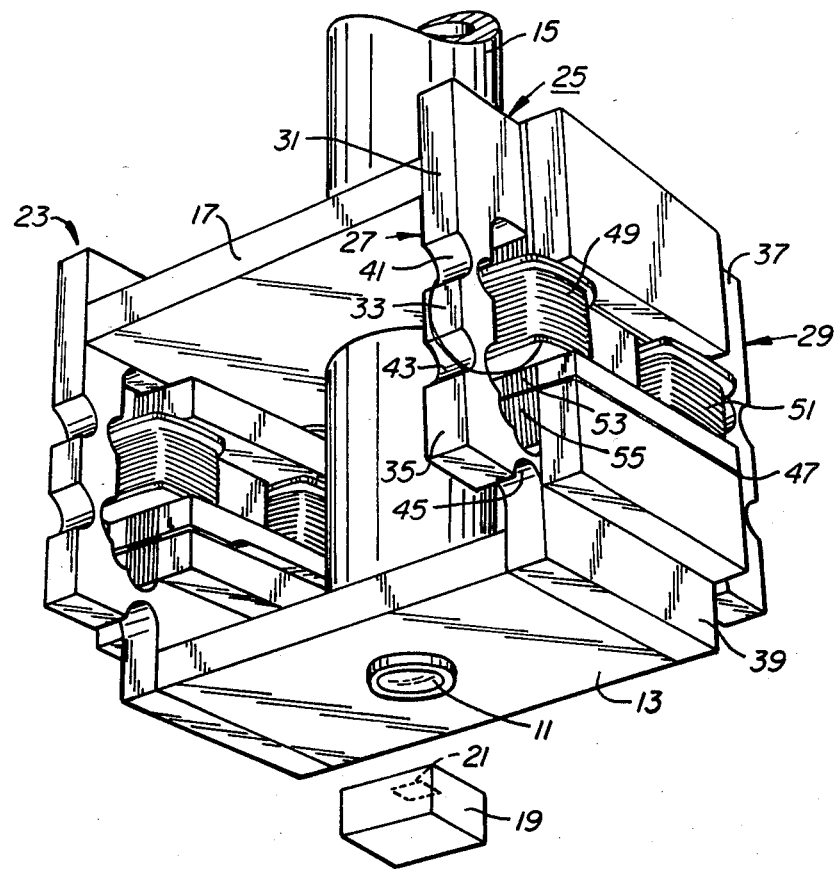
FIG._1.
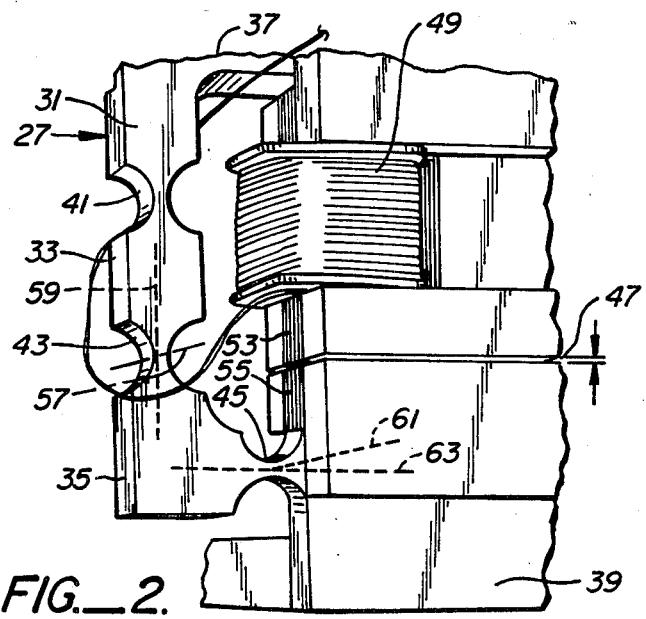
FIG._2.

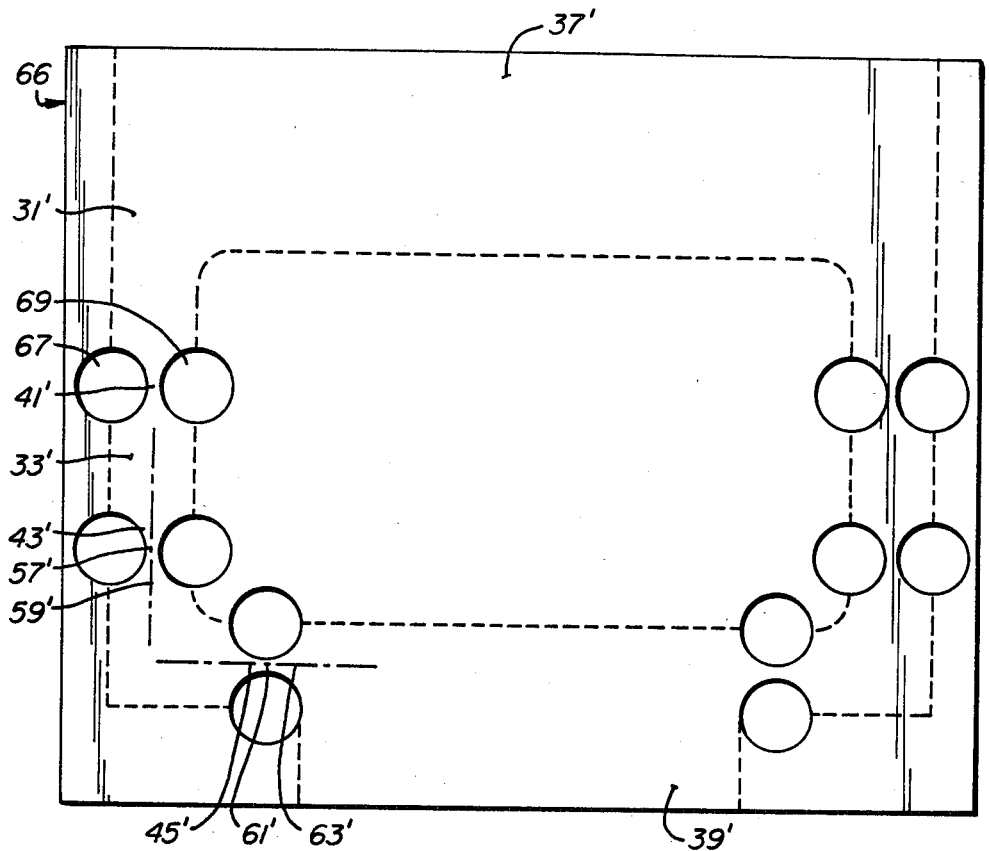
FIG._3.
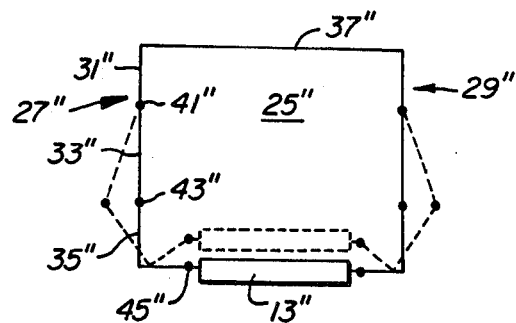
FIG._4.

SUPPORT MECHANISM UTILIZING FLEXUAL PIVOTS

BACKGROUND OF THE INVENTION

This invention relates generally to mechanisms for supporting objects in a manner to permit small movement of them with very high precision control.

There are many applications where the movement of an object over a very small distance (such as 1/1000th of an inch or less) is desirably made with a high degree of controllability and smoothness. A primary application for such mechanisms is found in various optics arrangements. The focusing of a lens or the positioning of a mirror, that are part of an optical system, are examples, particularly in precision or coherent optical systems. Another example is in the precision cutting of objects where a cutting blade position must be controlled within very close tolerances over a small distance, such as with surgery applications.

Therefore, it is a primary object of the present invention to provide a mechanism which supports and allows such very small controllable movement of objects with a very high degree of precision and smoothness.

It is another object of the present invention to provide such a mechanism that is simple and inexpensive to manufacture with a high degree of reproducibility.

SUMMARY OF THE INVENTION

These and additional objects are accomplished by the various aspects of the present invention, wherein, briefly, an object that is to be so controlled as to position is held by a support that includes at least one flexual pivot with a means coupled to the object for applying smooth movement to it. If such an object is held on either side thereof by a pair of such supports having a plurality of such flexual pivots along the length of the support, the motion imparted to the object will additionally maintain its orientation with respect to its surroundings and without imparting a bending moment to the remaining portions of the support member between the flexual pivots.

Each such support is preferably made of a continuous piece of elastic material having cross sectional dimensions along most of its length that resist bending when the forces contemplated for application into the object so supported are applied to that object. The flexual pivots are formed, according to one aspect of the invention, by reducing the thickness in at least one direction of the support at each position where such a pivot is desired. This reduced thickness is made to be small enough for the particular material utilized to provide the necessary bending when the forces contemplated for application to the object are so applied. A preferred method of manufacturing such a support is to first form in a blank piece of sheet material the reduced thickness portions between adjacent pairs of holes that are first formed in the sheet material. The support member is then cut from the sheet material at its desired finished edges which pass through these holes first formed in the sheet material.

Additional objects, advantages and features of the various aspects of the present invention will be better understood from the following description of a preferred embodiment thereof, which description should be taken in conjunction with the accompanying drawings.

BRIEF DESCRIPTION OF THE DRAWINGS

FIG. 1 shows an application of the support mechanism of the present invention for focusing a microscope;

FIG. 2 is an enlarged view of a portion of the mechanism FIG. 1;

FIGS. 3 illustrates a method of forming the supports with flexual pivots that are used in the mechanism of FIGS. 1 and 2; and FIG. 4 is a schematic diagram which illustrates the operation of the supports with flexual pivots that are utilized in the mechanism of FIGS. 1 and 2.

DESCRIPTION OF A PREFERRED EMBODIMENT

In order to adequately illustrate the features and advantages of the flexual pivot support structure according to the present invention, an example utilizing such a structure is described in some detail. Referring to the drawings, a mechanism for focusing a microscope objective 11 is described. A rectangular flat plate carrier 13 supports the objective lens element 11 without any motion there between. A remaining portion 15 of the microscope has a support member 17 fixedly attached thereto. There is no attachment between the objective lens 11 and carrier 13, on the one hand, with the main microscope portion 15 and support plate 17, on the other hand, except through the flexual pivot support elements to be described below.

It is helpful in understanding the present invention to describe briefly a particular application of an optical focusing mechanism in which the flexual pivot structural member invention is utilized. Referring to FIG. 1, the example there shown includes an object support 19 having a very smooth top surface upon which an object 21 to be viewed lies. Such an object 21 can be an integrated circuit wafer that is either finished or in the middle of its processing steps. As part of semi-conductor fabrication technology, it is necessary to maintain the width of lines on the circuit chip within certain tolerances. This is particularly becoming more strigent as the size of the integrated circuit chips is being reduced, thus leaving less room for error in the circuit chip manufacturing process. The circuits to be viewed by the microscope do have some significant surface variation and because of the large magnifications necessary, the depth of field of the microscope is often 0.1 micron or less. This, therefore, requires carefully movement of the object lens 11 over very small distance, often less than 1/1000th of an inch, and can even be as small as 0.000001 inch or less. An application of the flexual pivot support mechanism of the present invention to an instrument for measuring such integrated circuit line widths is additionally considered to be part of this invention. In such an instrument, the entire mechanism, including the carrier 13 and support plate 17, are moved together with respect to the object support 19 to effect rough focusing, the fine focusing being effected by the mechanism shown in the figures.

The carrier 13 is attached to the support plate 17 only through substantially identically shaped supports 23 and 25. Referring to the support 25 as exemplary, it includes two vertically oriented support elements 27 and 29 which are shaped substantially identically but are oriented oppositely. Referring to the support element 27 as an example, a continuous material piece contains large cross sectional portions in the form of an upper arm 31, a middle arm 33 and a lower arm 35. The material and cross sectional dimensions of these arm portions of the support 27 are made sufficient so they do not bend under the application of force required to move the carrier 13 over a defined small distance. The upper arm 31 is attached to a horizontal element 37 which connects the two supports 27 and 29 at their tops. Similarly, a horizontal element 39 connects the two supports 27 and 29 at their bottom and is also connected to one end of the carrier 13.

Three flexual pivots are provided as part of each support arm, the support arm 31 being exemplary. Pivots 41, 43 and 45 are formed by reducing the cross sectional dimension of the material to a thickness where it will bend at those pivots in response to the force available to be applied to move the carrier 13 over its defined distance of travel. The thickness of the support arm 27 is reduced in only one dimension in order to confine the bending of the element to one direction but it could be alternatively reduced in both directions to form a pivot that is moveable in a 360 degree pattern. Further, a plurality of single direction pivots can be provided, as another alternative, in various different directions as part of a single support element. For the particular example being described, however, it is desirable to confine such movement in the plane of the flat end support element 25.

A gap 47 defines the maximum distance of travel permitted by the carrier 13 with respect to the support plate 17. In order to provide the motion, a pair of electro-magnetic coils 49 and 51 is provided on a laminated core 53 of magnetic material. This structure is attached to the upper support plate 17. A laminated magnetic pole face 55 is positioned on the under side of the gap 47 and is attached to the bottom horizontal member 39 of the end support member 25. The same structure is provided in conjunction with the support end member 23 at the opposite side of the mechanism. The level of electrical current applied to the magnetic coils (4 in total) determines the position of the carrier 13 with respect to the support plate 17. An increase in the level of electrical current in these coils will cause the gap 47 to narrow, a reduction of electrical current causing the gap to increase by the elastic nature of the material from which the flexual pivots are formed. A gap 47, for the semiconductor wafer microscope application, is typically 0.001 inch at its maximum rest position but can be anything within a wide range of gaps for this and other applications.

The use of flexual pivots, rather than hinges, allows careful and smooth movement over small distances. There is no static friction and displacement is directly proportional to the force applied. In this case, the force and displacement are directly proportional to the magnetic flux. The motive force must be selected to be of a type to avoid any sliding between mechanical pieces or other arrangements that would cause discontinuous motion. The use of an electro-magnetic structures for the application of the motive force satisfies this requirement and is particularly suitable for easy control, such as from a computer system. All of the parts shown in the figures, except for the magnetic pole faces such as the laminated elements 53 and 55, are necessarily made of a non-magnetic material, aluminum having been found as having desirable mechanical and structural characteristics as well. For other applications, different kinds of motive sources may be employed, another being a pneumatic bellows connected directly to move the carrier 13, which has the desirable non-sliding characteristics.

As best illustrated by reference to FIG. 2, the placement of the flexual pivots along the support arm 27 in this particular embodiment will be explained. The pivot 43 can be considered having an axis of rotation 57 about which the rotation of adjoining segments 33 and 35 occurs, and a longitudinal axis 59, both axes intersecting in the middle of the reduced thickness pivot portion 43. Similarly, axis 61 of rotation and longitudinal axis 63 can be viewed as associated with the pivot 45. Because of the single bending direction intentionally built into each of the pivots, as describes previously, all of the axes of rotation, such as the axes 57 and 61, are parallel to each other.

The particular arrangement of three pivots, as best illustrated in FIG. 2, causes the carrier 13 to remain parallel with itself as it is moved. The orientation of the longitudinal axis 63 of the pivot 45 is oriented orthogonally with the vertically oriented longitudinal axes of the other two pivots 41 and 43. By providing two such pivots on the vertical portion of the "L" shaped support arm 27, there is no bending of the upper enlarged cross sectional portion 31 and it thus may remain fixed in position.

Movement of the device as the gap 47 is closed is schematically illustrated in FIG. 4 wherein the solid lines are used to represent the rest position of the elements included, the dotted outline the position of deflection when electrical current is applied to the electromagnets, and the elements are indicated by reference numbers similar those used in FIG. 2 but with a double prime (") added thereto.

A preferred process of making the support end plate 25 is illustrated with respect to FIG. 3, wherein parts corresponding to those of FIGS. 1 and 2 are indicated by the same reference numbers with a prime (') added thereto. The first step of the process is to form a plate 66 into a desired initial shape from a selected material. Any desired variations in thickness would be imparted by this first step but in the embodiment being described it is preferable to make the starting plate 66 have a substantially uniform thickness throughout and be rectilinear in shape. The thickness is that which the finished support plate 25 is to have. The solid material plate 66 then has a plurality of pairs of holes drilled in it, such as the pair of holes 67 and 69. The space left between the holes is carefully controlled to have the thickness desired for the pivot 41. Similarly, other pairs of holes are formed in the plate 66 to make other of the pivots. After all of the pivots are so formed, the plate 66 is cut along the lines indicated in FIG. 3 in dashed outline to form a finished end support piece 25 as illustrated in FIGS. 1 and 2. The advantage of this technique is that the pivots are formed in a simple and inexpensive, but precise, manner. The technique is particularly adapted for manufacture of the plate 25 by automatic equipment such as numerical controlled machine tools.

The material selected for the plate 56 in the specific example described with respect with FIGS. 1 and 2 is preferred to be aluminum. Whatever material is selected, it should have a moderately high modulus of elasticity so that the pivots will restore the element to its rest state after any deflecting forces are removed from it. The material should also be characterized by having a high differential rate of bending for a given moment as a function of its thickness so that the pivot portions will give the desired flexibility to a given moving force while the portions adjacent to each pivot having a larger cross sectional area will not contribute to the bending, thus allowing the bending characteristics of the support to be carefully placed and controlled for a particular application.

Although the various aspects of the present invention have been described with respect its preferred embodiment, it will be understood that the invention is entitled to protection within the full scope of the appended claims.

It is claimed:

1. A mechanism supporting a first member with respect to a second member in a manner permitting smooth and controllable motion therebetween over a small distance, comprising a pair of supports connected to said members at spaced apart locations, each of said supports including three flexual pivots therealong, two oriented in a direction extending between said members and the other extending in a direction substantially orthogonal thereto, whereby said first and second members maintain a parallel relationship with each other and ends of said supports remain straight as the members are moved over said small distance.

2. A system for moving a carrier over a small distance with respect to a base member, comprising:

at least a pair of supports connected between said carrier and said base member at spaced apart locations, each of said pair of supports including a single piece of elongated material of a particular cross-sectional dimension chosen for it to be rigid in all dimensions over its entire length except for a plurality of locations therealong wherein its cross section is narrowed in at least one direction in order to provide enough flexibility at those locations to allow said carrier to be moved over said small distance, means operably connected to said carrier for smoothly and controllably moving said carrier over said small distance, and, wherein, the narrowed cross-sectional locations are at least three in number, two of the three narrowed portions being oriented in a direction extending between the carrier and the base member and the other extending substantially orthogonally thereto, whereby said carrier maintains a parallel relationship with said base member and ends of supports remain straight as the carrier is moved over said small distance.

* * * * *